US006030346A

United States Patent [19]

Buck et al.

[11] Patent Number: 6,030,346

[45] Date of Patent: Feb. 29, 2000

[54] ULTRASOUND IMAGING PROBE ASSEMBLY

[75] Inventors: Arthur Glen Buck, Sherwood; Ronald A. Olson, Portland, both of Oreg.

[73] Assignee: The Whitaker Corporation, Wilmington, Del.

[21] Appl. No.: 09/069,786

[22] Filed: Apr. 29, 1998

Related U.S. Application Data

[63] Continuation-in-part of application No. 08/926,913, Sep. 10, 1997, Pat. No. 5,834,699, which is a continuation of application No. 08/604,690, Feb. 21, 1996, abandoned

[60] Provisional application No. 60/066,779, Nov. 25, 1997.

[51] Int. Cl.[7] .......... A61B 8/00

[52] U.S. Cl. .......... 600/459

[58] Field of Search .......... 174/75 C, 102 R, 174/103–105, 107–108, 128.1, 128.2; 600/437, 443, 459, 462–463

[56] References Cited

U.S. PATENT DOCUMENTS

| | | | |
|---|---|---|---|
| 1,009,030 | 11/1911 | Frederick . | |
| 1,348,033 | 7/1920 | Moon . | |
| 1,691,869 | 11/1928 | Fowle . | |
| 2,212,927 | 8/1940 | Baguley . | |
| 2,913,514 | 11/1959 | Short | 174/90 |
| 3,240,867 | 3/1966 | Maddox | 174/69 |
| 3,291,898 | 12/1966 | Sandell | 174/131 |
| 3,351,706 | 11/1967 | Gneree | 174/105 |
| 3,484,532 | 12/1969 | Anderson | 174/36 |
| 3,602,632 | 8/1971 | Ollis | 174/36 |
| 3,629,941 | 12/1971 | Wagele | 174/105 |
| 3,649,744 | 3/1972 | Coleman | 174/107 |
| 3,651,243 | 3/1972 | Hornor et al. | 174/34 |
| 3,676,576 | 7/1972 | Dubernet et al. | 174/113 R |
| 3,784,732 | 1/1974 | Whitfill, Jr. | 174/108 |
| 3,829,603 | 8/1974 | Hansen et al. | 174/115 |
| 4,358,636 | 11/1982 | Ijff et al. | 174/103 |
| 4,440,974 | 4/1984 | Naudet | 174/108 |
| 4,461,923 | 7/1984 | Bogese, II | 174/36 |
| 4,552,989 | 11/1985 | Sass | 174/103 |
| 4,677,418 | 6/1987 | Shulver | 338/214 |
| 4,691,081 | 9/1987 | Gupta et al. | 174/105 |
| 4,694,122 | 9/1987 | Visser | 174/106 R |
| 4,840,563 | 6/1989 | Altendorf | 433/29 |
| 4,841,977 | 6/1989 | Griffith et al. | 600/439 |
| 5,212,350 | 5/1993 | Gebs | 174/102 R |
| 5,220,130 | 6/1993 | Walters | 174/36 |
| 5,368,037 | 11/1994 | Eberle et al. | 600/463 |
| 5,423,220 | 6/1995 | Finsterwald et al. | 73/642 |
| 5,456,259 | 10/1995 | Barlow et al. | 600/463 |
| 5,491,299 | 2/1996 | Naylor et al. | 174/36 |
| 5,521,333 | 5/1996 | Kobayashi et al. | 174/113 R |
| 5,523,528 | 6/1996 | Bese et al. | 174/36 |
| 5,552,565 | 9/1996 | Cartian et al. | 174/117 F |
| 5,559,388 | 9/1996 | Lorraine et al. | 310/334 |

FOREIGN PATENT DOCUMENTS

| | | | |
|---|---|---|---|
| 276974 | 1/1988 | European Pat. Off. | H01B 7/04 |
| 2254862 | 12/1974 | France | H01B 7/18 |
| 3220392A1 | 5/1982 | Germany | H01B 7/18 |

*Primary Examiner*—Francis J. Jaworski

[57] ABSTRACT

An ultrasound imaging probe assembly (1*a*) has multiple piezoelectric elements (3) producing an array of scanned ultrasound signals and being connected by insulated conductors (4) to an electronic scanner to convert the signals to an image, the insulated conductors (4) and an uninsulated conductor (15) are concentric with an inner conductor (8) and a conducting shield (7), and the insulated conductors (4) are capacitively coupled to the inner conductor (8) and the shield (7) to provide an ultrasound transducer assembly (1) of compact size.

8 Claims, 2 Drawing Sheets

ULTRASOUND IMAGING PROBE ASSEMBLY

CROSS REFERENCE TO RELATED APPLICATIONS

This application is a continuation in part of application Ser. No. 08/926,913 filed Sep. 10, 1997 U.S. Pat. No. 5,834,699, in turn, a continuation of application Ser. No. 08/604,690, filed Feb. 21, 1996, abandoned. This application claims the benefit of provisional application 60/066,779, filed Nov. 25, 1997.

FIELD OF THE INVENTION

The invention relates to an ultrasound imaging probe assembly, and more particularly, to an ultrasound imaging probe having a transducer assembly with a dense array of piezoelectric elements generating a sequenced or phased array of ultrasonic pulsed signals for imaging, and diagnosis of, body organs and tissue.

BACKGROUND OF THE INVENTION

A technical paper by, M. Grenstein, P. Lum, H. Yoshida, M.S. Seyed-Bolorforosh, "A 2.5 MHz 2-D Array With Z-axis Backing", IEEE Ultrasound Symposium, San Antonio, Tex., Nov. 3, 1996, describes an array of high density piezoelectric elements that are useful in an ultrasound imaging transducer assembly, the piezoelectric elements generating a sequenced or phased array of ultrasonic pulsed signals in separate signal channels. The transducer assembly comprises a front of an ultrasound imaging probe assembly that is manipulated to probe a desired portion of the body of a medical patient. The transducer assembly generates pulsed ultrasonic signals that are reflected by the probed portion of the body, the reflected signals are transmitted to an electronic medical apparatus, which is an electronic apparatus that scans the signals to produce an electronically generated image of the portion of the medical patient that is being probed. The piezoelectric elements of the ultrasonic imaging probe assembly are individually connected via a backing material to individual, signal transmitting, circuits.

Various forms of backing material are described in, Kremkau, Frederick W., *Diagnostic Ultrasound*, W. B Saunders Co., Philadelphia, Pa. 1993. In a patented probe, described in U.S. Pat. No. 5,482,047, the piezoelectric elements of the ultrasound imaging probe assembly are individually connected, via circuitry, to individual wires of an electrical cable. The individual wires are coaxial cables that transmit the pulses and the reflected signals between the probe assembly portion of the probe and the electronic medical apparatus. According to U.S. Patent Application, Serial No., unknown, filed Oct. 29, 1997, and claiming the benefit of provisional application 60/032,769, Filed Dec. 11, 1996, piezoelectric elements of the ultrasound imaging probe assembly are individually connected by circuitry on a flexible printed circuit, and from there, to signal transmitting conductors of individual coaxial cables.

A main objective is to produce a large number of signals in an imaging transducer assembly of an ultrasound imaging probe assembly of limited size to increase the density of the signals, and, hence, to increase the resolution of the image.

In the past, coaxial shielding has been necessary to prevent unacceptable levels of cross talk among the signal transmitting conductors. Each of the signal transmitting conductors is concentrically encircled by a conducting shield, to comprise a coaxial cable. A major cost of manufacturing coaxial cables resides in the consumption of time and materials for applying the shield on each coaxial cable.

SUMMARY OF THE INVENTION

The problem to be solved by the invention is to provide an ultrasound imaging probe wherein cross talk among signal trnasmitting conductors of the probe is reduced without surrounding each of the conductors with its own individual shielding.

It would be advantageous in an imaging transducer assembly of an ultrasound imaging probe assembly to provide reduced cross talk among signal transmitting conductors without surrounding each of the conductors with its own individual shielding to achieve substantial compactness of the probe assembly. It would be further advantageous to provide a probe assembly that is flexible and limp and adapted to be hand held and maneuvered for monitoring human physiological indications.

The invention achieves a reduction in size and a reduction in cross talk among signal carrying insulated conductors of an imaging transducer assembly of an ultrasound imaging probe assembly that is flexible and limp, and adapted to be hand held and maneuvered, the insulated conductors being capacitively coupled to a conducting shield of limp flexible construction that encircles each of the insulated conductors in the same row, and by the insulated conductors in a first row being capacitively coupled to a conducting member that they encircle. According to an embodiment, the shield and the conducting member are concentric and at the same electrical potential by being electrically commoned to one another.

These conductors are not only smaller, but are fabricated of lower tensile strength metals that are less expensive than metals of relatively high tensile strength, due to the probe assembly having a tension resisting, conducting member that is encircled by the signal carrying conductors.

The problem to be solved by the invention is to provide an ultrasound imaging probe assembly wherein cross talk among signal carrying conductors of an ultrasound transducer assembly of the probe assembly is reduced without surrounding each of said conductors with its own individual shielding.

According to an embodiment, the insulated conductors are together in a row, and the row helically encircles the conducting member.

DESCRIPTION OF THE DRAWINGS

Embodiments of the invention will now be disclosed by way of example with reference to the accompanying drawings, according to which.

DETAILED DESCRIPTION

Figure 1:
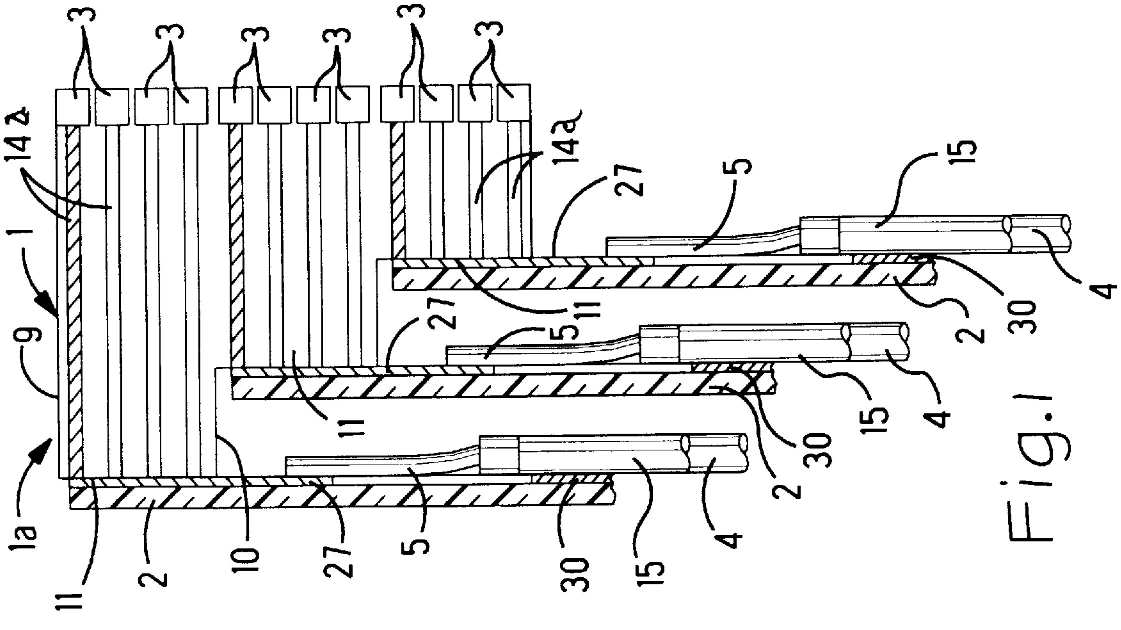
FIG. 1 is a side view in section of a portion of an ultrasound transducer assembly of an ultrasound imaging probe assembly, wherein, piezoelectric elements are electrically connected to insulated conductors.

With reference to FIG. 1, an imaging transducer assembly 1 of an ultrasound imaging probe assembly 1*a* comprises, circuitry 2 electrically connecting rows of piezoelectric elements 3 to signal transmitting, insulated conductors 4. The probe assembly 1*a* is hand held and manipulated to position the imaging transducer assembly 1 at a desired location on a medical patient. Pulsed ultrasound signals are transmitted along the assembly 1 to a medical instrument comprising, apparatus that scans the signals to produce an electronically generated image of a portion of the medical patient that is being probed. A main objective is to produce a large number of sequenced or phased array signals in an assembly 1 of limited size to increase resolution of the image.

The array of piezoelectric elements 3 provide phased or sequenced voltage pulses having ultrasonic frequencies typically in the range of 2.5 to 10 MHz. Pulses with frequencies as low as 2 MHz and as high as 30 MHz are not uncommon. The array of piezoelectric elements 3 may be arranged in a matrix of 50×50 wherein 2500 of the piezoelectric elements 3 are one-half acoustic wavelength apart, for example, on pitch spacings in a range of 4 mil. pitch to 12 mil pitch.

The piezoelectric elements 3 are mounted against a backing layer 9, developed as a wide variety of adhesive epoxy materials having a wide variety of fillers, that eliminate cross talk among the piezoelectric elements 3. Further details of an array of piezoelectric elements 3 are described in a technical paper by, M. Greenstein, P. Lum, H. Yoshida, M. S. Seyed-Bolorforosh, "A 2.5 MHz 2-D Array With Z-Axis Backing," IEEE Ultrasonic Symposium, San Antonio, Tex., Nov. 3, 1996. Further desired properties of backing materials 9 are known, for example, as described by, Kremkau, Frederick W., *Diagnostic Ultrasound*, W. B. Saunders Co., Philadelphia, Pa. 1993.

The piezoelectric elements 3 typically originate from a wafer of a known, high purity PZT polycrystalline piezoelectric material. Electrical connections are made to allow each element to be electrically stimulated for mechanical pulse generation, and to produce electrical signals upon stimulation by return echoes.

With reference to FIG. 1, the backing layer 9 can 35 be molded or machined on a back side 10 thereof with one or more steps. The steps have risers 11 corresponding to the side-to-side spacing of elements 3. Circuitry 2 can be made thin enough to not exceed the step height, typical of diagnostic ultrasound, with circuit trace centerlines as closely spaced as 4 mils on a flexible printed circuit. For example, the steps can be made in increments of 4 mil. height, measured from one step to another. The printed circuit having the circuitry 2 thereon, is manufactured by etching an insulating substrate, to produce circuit traces 27 spaced apart on a pitch spacing as low as 4 mil. pitch spacing. The backing layer 9 comprises a solid layer that is attached to the piezoelectric elements 3 to provide electrical signal paths in separate signal channels. The backing layer 9 provides acoustic attenuation for the signal channels. A particular goal of the backing layer 9 is to provide for maximum density of the piezoelectric elements 3 in a material of desired acoustic properties. A further goal of the backing layer 9 is to provide a high density of electrical interconnections for establishing separate signal channels from the piezoelectric elements 3 through the backing layer 9 to provide an array of both acoustically separate and electrically separate signal channels that can be electrically connected to the signal transmitting conductors 4. Further details of construction of the piezoelectric elements 3 are disclosed in U.S. patent application, Ser. No. 08/959,870, filed Oct. 29, 1997, and claiming the benefit of provisional application 60/032,769, Filed Dec. 11, 1996, the disclosure of which is herein incorporated by reference.

According to an example, imbedded conductors 14*a* in the backing layer 9 are to be connected via the insulated conductors 4 to an apparatus, for example, an external electronic scanner for conversion of scanned signals into an image of the probed area of a medical patient.

Circuitry 2 can be manufactured by etching circuit traces 27 spaced apart on a pitch spacing as low as 4 mil. pitch spacing. For example, a 4 mil. thick polyimide film coated with copper on one side is photoetched to selectively remove the copper, forming a row of circuit traces 27 extending transversely of an edge 28 of the circuitry 2. The circuit traces 27 can extend to a row of spaced apart, conducting pads 29 to be connected to metal wire, center conductors 5 of respective insulated conductors 4. An elongated ground bus 30 extends parallel to the row of conducting pads 29.

According to an embodiment of the invention, with reference to FIG. 1, the backing layer 9 can be molded or machined on a back side with one or more steps. The steps are separated by the respective risers 11 in incremental heights corresponding to the element 3 spacings, measured from one step to another.

With reference to FIG. 1, a portion of an array of piezoelectric elements 3 is shown with multiple rows or array patterns that are not necessarily in neat rows of such elements 3. The elements 3 can be on even or irregular spacings apart. For the purposes of illustration, FIG. 1 shows a portion of the total number of rows of, or spacings between, piezoelectric elements 3 in the array. The backing layer 9 on the back side is stepped with multiple risers 11, one for each row or spacing apart of piezoelectric elements 3. Each riser 11 is offset inwardly along a corresponding step, and offset inwardly from a previous riser 11 to expose at least one row, or one stepped spacing apart, of imbedded conductors 14*a* along a step that is between successive risers 11. In FIG. 1, three rows of, or three stepped spacings apart of, imbedded conductors 14*a* are exposed along each step.

In FIG. 1, the imbedded conductors 14*a* of each exposed row of such conductors 14*a* extend to a riser 11, with each riser 11 being offset inwardly from a previous riser 11 to expose multiple arrays that comprise rows or other arrays of imbedded conductors 14*a*. A row array or a stepped spacing array of circuit traces 27 on the printed circuit 2 register against a corresponding row, or corresponding array of, imbedded conductors 14*a*, and are electrically connected to such respective conductors 14*a* by solder, for example. The adjacent riser 11 provides a stop for the edge 28 of the printed circuit 2. The adjacent riser 11 further separates the printed circuit 2 from another row or array of exposed conductors 14*a* to be connected to a corresponding row or array of circuit traces 27 on another printed circuit 2. The assembly 1 can be limited in size, by eliminating the need for a coaxial shield to encircle each signal transmitting conductor 4.

In the past, each of the coaxial cables can be made slender, in the order of 38–60 American Wire Gauge conductors, encircled concentrically by dielectric of polytetrafluoroethylene having an overall diameter of 0.015–0.0177 inch, concentrically encircled by a conducting, served shield of 80% coverage, i.e. braided wires of 44 American Wire Gauge that are braided to cover 80% of an area with the wires. The shield on each of the coaxial cables reduces cross talk in the signal carrying conductors. The shield on each of the coaxial cables increases the size and cost of the probe assembly 1*a*, and requires individual electrical connection to a ground or earth electrical potential. The invention provides improved compactness of the imaging transducer assembly 1 of an ultrasound imaging probe assembly 1*a* by a high density of signal transmitting conductors that attain a reduction in cross talk without an individual shield on each of the insulated conductors 4.

Figure 3:
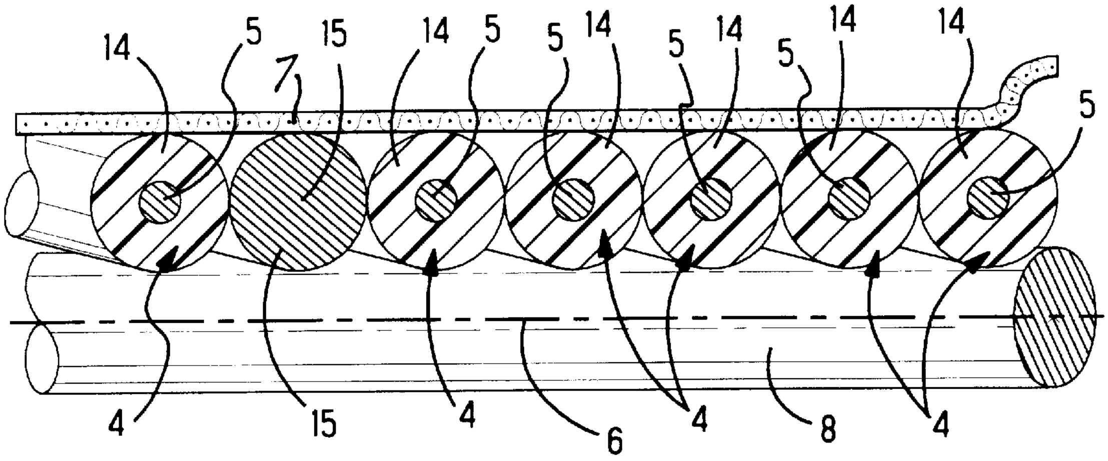
FIG. 3 is an end view of signal transmitting conductors of the probe assembly, as shown in FIG. 1.

Each of the insulated conductors 4 is constructed with a center conductor 5 concentrically surrounded by dielectric 14. The insulated conductors 4 are arranged in at least one concentric row, FIGS. 3 and 4, with each concentric row of insulated conductors being concentric with an inner conductor 8, and with each concentric row of insulated conductors 4 engaging and being concentric with an encircling, conducting shield 7. A first, inner row of insulated conductors 4 concentrically encircles an inner conductor in the form of the uninsulated conductor 8 extending along a central axis 6. Each successive, concentric row of insulated conductors 4, FIG. 4, for example, concentrically encircles an inner conductor in the form of the conducting shield 7 that is concentric with and encircles a previous row of insulated conductors 4.

Figure 4:
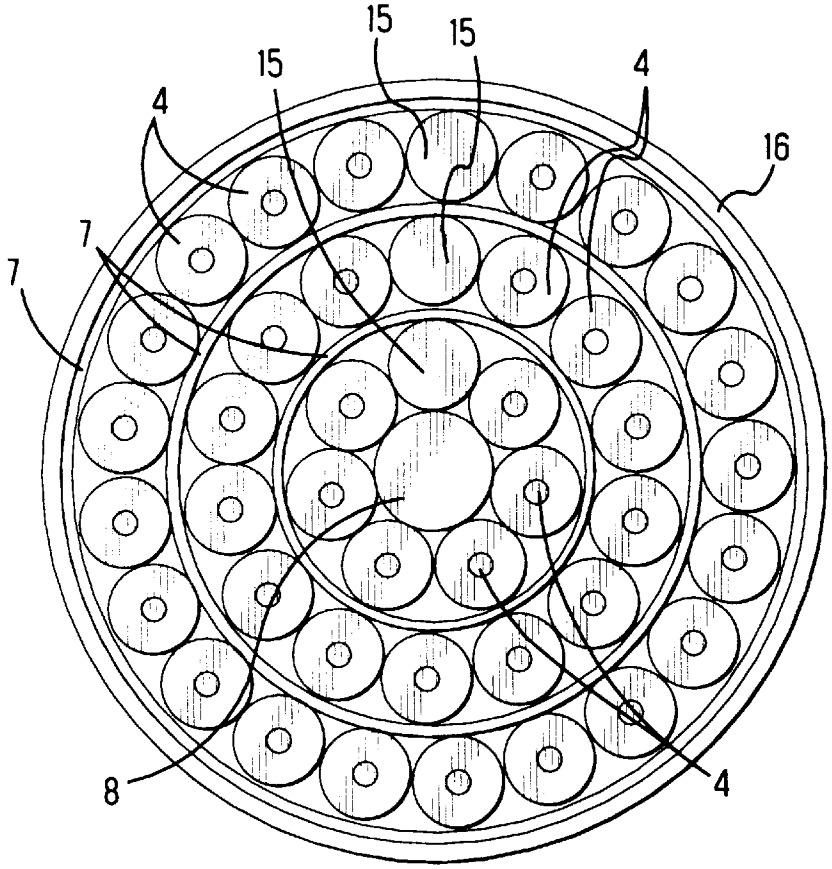
FIG. 4 is an end view of another embodiment of the signal transmitting conductors of the probe assembly, as shown in FIG. 1.

The insulated conductors 4 in the same row engage and capacitively couple to the encircling shield 7 and to the encircled inner conductor 8 or 7 that is encircled by the insulated conductors 4 in the same row. The insulated conductors 4 in the same row helically extend side by side in the same row along the axis 6 to remain engaged and capacitively coupled to the encircling shield 7 and to the encircled inner conductor 8 or 7, despite flexure of the insulated conductors 4 in a variety of directions during manipulation of the transducer assembly 1 to a desired location against a medical patient. At least one flexible and limp, uninsulated conductor 15 is side by side with the insulated conductors 4 in the same row. The uninsulated conductor 15 is electically connected to the ground bus 30, for example, by solder. The conductors 4 and 15 in the same row helically extend along the axis 6 to remain in contact against the helically encircled conductor 8 or 7 and the encircling shield 7, despite flexure of the row of conductors 4 and 15 in a variety of directions. As shown in FIG. 4, a flexible and limp outer jacket 16 encircles the shield 7 that engages the outermost row of conductors 4 and 15.

To enable a limp and flexible construction for ease in such manipulation, the conductors 4 and 15 helically extend, and are free of compression against one another in the same row, and are free of compression against the encircling shield 7, and are free of compression against the encircled conductor 8 or 7.

FIG. 4 shows a transducer assembly 1 with multiple, successive rows comprised of conductors 4 and 15. Each row encircles an inner conductor 8 or 7. Each row is encircled by a conducting shield 7.

The central conductor 8 is tension resisting, which eliminates a requirement that the insulated conductors 4 be high tension resistant. The cost of tension resistant metal alloys is more than that of less tension resistant metal alloys. The insulated conductors 4 comprise less expensive, lower tension resistant, metal alloys.

Thus, each of the embodiments has at least one row of conductors 4 with each corresponding row being encircled by a conducting shield 7. Each row is concentric with a corresponding encircling shield 7, and each row concentrically encircles a corresponding inner conductor 8 or 7 that comprises either the central conductor 8 or one of the shields 7.

With respect to each embodiment, at least one uninsulated conductor 15 is in the same corresponding row with the insulated conductors 4. Further, with respect to each embodiment, the insulated conductors 4 and each uninsulated conductor 15, in the same corresponding row, are enclosed within an encircling conducting shield 7.

All of the conductors 4 and 15 in the same corresponding row are free of compression against one another to allow or promote their undergoing individual flexure when the cable 1 undergoes flexure in a variety of directions. A gap in any of the encircling rows of conductors 4 and 15 is allowed. For example, when the conductors 4 and 15 engage one another side to side in the corresponding encircling row, a gap in such encircling row is permitted. The gap has a width less than the diameter of each of the conductors 4 and 15 to prevent movement of any one of the conductors 4 and 15 out of its position, in order, within the corresponding row.

Similarly, each of the conductors 4 and 15 in the row extends helically and in contact with an interior surface of the corresponding shield 7 to remain in contact with the shield 7, despite flexure of the shield 7 in a variety of directions when the assembly 1 undergoes flexure.

The encircling shield 7 resists movement of each of the helically extending conductors 4 and 15 from out of its position within the helically encircling row. However, the interior of the shield 7 contacts the conductors 4 and 15 while being free of compression radially against the conductors 4 and 15, which allows the conductors 4 and 15 to move relative to the shield 7 and relative to the encircled conducting member 8, as the conductors 4 and 15 undergo individual flexure. The shield 7 defines an inner circumference within which movement of the corresponding row of conductors 4 and 15 is restricted, while said conductors 4 and 15 undergo individual flexure during flexure of the assembly 1. The shield 7 restricts movement of the conductors 4 and 15 within close proximity to both the conducting member 8 and the conducting shield 7.

The conductors 4 and 15 are free to undergo individual movement and flexure, and are free to slip while remaining engaged against both the corresponding conducting member 8 or 7 and the corresponding shield 7. Thereby, limpness during flexure is assured to permit freedom of manipulation of the transducer assembly 1. Further, the conductors 4 and 15 remain in physical contact with the conducting member 8 or 7, and remain in contact with the shield 7, despite flexure in a variety of directions. A reduction in cross talk is achieved among the signal carrying insulated conductors 4 without shielding on individual insulated conductors 4. Elimination of such shielding provides a compact transducer assembly 1. Further, the signal transmitting conductors 4 are flexible and limp and adapted to be hand held and maneuvered easily by flexure in a variety of directions.

Figure 2:
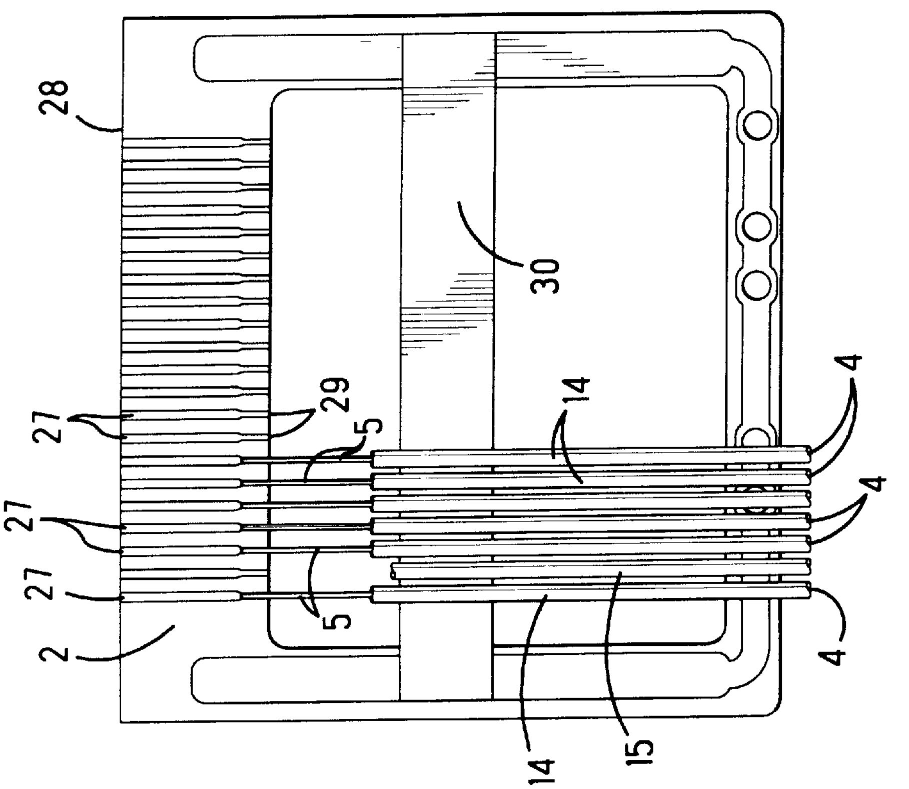
FIG. 2 is top view of the insulated conductors as shown in FIG. 1 being electrically connected to electrical circuitry.

With reference to FIGS. 2 and 4, the uninsulated conductor 15 is between a pair of the insulated conductors 4 that are side by side in the same row with the uninsulated conductor 15. The conductors 4 and 15 are arranged side by side in order, which is the same order that corresponds to the row being spread apart and arranged in a flat configuration for connection to the circuit traces, FIG. 2.

Said pair of insulated conductors 4, that are adjacent to the uninsulated conductor 15, are not only capacitively coupled to the encircled corresponding conductor 8 or 7, but are further capacitively coupled to the adjacent uninsulated conductor 15. Excluding such pair from the remaining insulated conductors 4, the remaining insulated conductors 4 have substantially equal capacitive coupling to the encircled corresponding conductor 8 or 7, and to the encircling corresponding shield 7. Said pair of the insulated conductors 4 in each corresponding row can serve as spares to replace one or two remaining insulated conductor 4 in the same row that may become defective.

Internal strain, due to tension, on the insulated conductors 4 of the transducer assembly 1 is borne by the conductor 8 in the form of a wire, while the insulated conductors 4 can be limp and freed from excessive strain. Thus, the insulated conductors 4 can be smaller in diameter or reduced in tensile strength, as compared to previous coaxial cable constructions. For example, wire of silver plated copper, SPC, of solid gauge can be used as a less costly alternative to the use of conductors fabricated from higher strength copper alloys, and an insulated conductor 4 with a solid gauge, single strand conductor is smaller in diameter as compared to a larger conductor fabricated of multiple strands.

When the diameter of the conductor 8 is equal to a multiple of 1.31 times the diameter of each insulated conductor 4 and each uninsulated conductor 15, a maximum total number of seven of the conductors 4 and 15, having equal diameters, engage and encircle the conductor 8.

To determine the total number of conductors 4 and 15 in the row, or to increase a gap in the row of conductors 3 and 15, the diameter of the conductor 8 is increased until the conductors 4 and 15, having substantially similar diameters, in the encircling row engage the conductor 8, and the conductors 4 and 15 in the same row are side by side without close packing of the conductors 4 and 15 in compression against one another. With the conductors 4 and 15 engaging one another, a gap in the row of the conductors 4 and 15 is less than the diameter of one of the conductors 4 and 15 in the same row.

Each shield 7 is constructed, for example, as a limp and flexible, hollow cylindrical braid, or served shield, of 44 American Wire Gauge wires with 80% minimum coverage. The shield 7 is alternatively constructed of a limp and flexible laminate of conducting aluminum foil bonded to opposite sides of a flexible polyester tape as disclosed in U.S. patent application, Ser. No. 08/604,690, filed Feb. 21, 1996, abandoned, attorney docket no. 16329, and as disclosed in U.S. patent application Ser. No. 08/926,913, filed Sept. 10, 1997, attorney docket 16329A, incorporated herein by reference. One of the conducting foils of the shield 7 faces and engages the conductors 4 and 15 on an inner row. The other of the conducting foils of the shield 7 faces and engages the conductors 4 and 15 on an outer row. The shield 7 is laid over the insulated conductors 4 and 15 in the same row. The tape 9 having the foil 10 can be cylindrical with an overlapped seam. Alternatively the tape 9 with the foil comprises overlapping helices enclosing the row of adjacent conductors 4 and 15, the overlapped seam 12 overlapping the adjacent helices with one another. Alternatively, the combination of the tape 9 and foil 10 comprises a helically wrapped ribbon with open helices. The helices of the shield 7 have an opposite pitch with respect to the helices of the adjacent encircled row of conductors 4 and 15. Each successive row of conductors 4 and 15 can be laid in helices with alternating pitch directions or, alternatively, the same pitch directions, not shown.

During transmission of electrical signals along the insulated conductors 4, an electrical coupling influence, for example, capacitive coupling, is maintained between each helically wound, insulated conductor 4 and the encircling shield 7 that encircles and contacts the insulated conductors 4. An electrical coupling influence, for example, capacitive coupling, is maintained between each helically wound, insulated conductor 4 and the conductor 8 or 7 that is encircled and contacted by the insulated conductors 4, and each conducting shield 7 and the conducting member 8 are electrically connected by each corresponding uninsulated conductor 15, to obtain a reduction in cross talk among the insulated conductors 4. The provision of the uninsulated conductor 15 in each row, eliminates the need to connect the shield 7 to the ground bus 30. The central conductor 8 is free to continue past the corresponding circuitry 2 for connection to a tension resisting chassis of the tranducer assembly 1 that is commoned to ground or reference electrical potential. Each ground bus 30 is electrically commonned to ground or reference electrical potential. The shields 7 of each row of conductors 4 are electrically commonned to ground or reference electrical potential, such that each conductor 4 is substantially equally capacitively coupled to an encircled conductor 8 or 7, and to an encircling shield 7, to obtain a reduction in cross talk among the insulated conductors 4 without shielding on each of the individual conductors 4. The circuitry 2 can be provided in separate portions of polyimide film, wherein a separate polyimide film portion of the circuitry 2 is provided for each row of the conductors 4 and 15. Each row of the conductors 4 and 15 can be connected to a separate, duplicate, polyimide film portion of the circuitry 2. As shown in FIG. 2, the seven conductors 4 and 15 in the first row are shown as being connected to seven of the twenty-one circuit traces 27 of the circuitry 2. The circuitry 2 shown in FIG. 2 can be duplicated and electrically connected to a corresponding row of the conductors 4 and 15. A duplicate of the circuitry 2 has twenty-one circuit traces 27 to be electrically connected to the twenty-one conductors 4 and 15 in the third row, as shown in FIG. 4. The fourteen conductors 4 and 15 in the intermediate row can be connected to fourteen of the twenty-one circuit traces 27 on a duplicate of the circuitry 2 that is shown in FIG. 2.

Other embodiments and modifications are intended to be covered by the spirit and scope of the appended claims.

What is claimed is:

1. An ultrasound diagnostic probe assembly comprising:

multiple piezoelectric elements producing an array of scanned ultrasound signals, at least one row of insulated, signal transmitting conductors electrically connecting the piezoelectric elements to an electronic scanner that converts the signals to an image, at least one uninsulated conductor in said row together with said signal transmitting conductors, each of the signal transmitting conductors and said at least one uninsulated conductor being in contact with a flexible inner conductor, a flexible conducting shield encircling the signal transmitting conductors and said at least one uninsulated conductor, the shield defining an inner circumference within which the signal transmitting conductors and said at least one uninsulated conductor are free to move and to undergo flexure while the signal transmitting conductors engage the shield and the flexible inner conductor, the signal transmitting conductors tending to cross talk among themselves, the shield and the inner conductor being commoned together, circuitry between, first, the piezoelectric elements and, second, the signal transmitting conductors and said at least one uninsulated conductor, said at least one uninsulated conductor being connected to a ground bus on the circuitry to eliminate the need for connecting the shield to the ground bus, the signal transmitting conductors each engaging both the inner conductor and the shield while being free to move within said inner circumference, and the signal transmitting conductors each further being purposely capacitance coupled with both the inner conductor and the shield to reduce cross talk among themselves.

2. An ultrasound diagnostic probe assembly as recited in claim 1, wherein the signal transmitting conductors and said at least one uninsulated conductor extend helically over the flexible inner conductor.

3. An ultrasound diagnostic probe assembly as recited in claim 1, wherein the signal transmitting conductors and said at least one uninsulated conductor helically extend over the flexible inner conductor, and the shield extends helically and encircles the signal transmitting conductors and said at least one uninsulated conductor.

4. An ultrasound diagnostic probe assembly as recited in claim 1, and further comprising:

at least a second row of insulated, signal transmitting conductors electrically connecting respective piezoelectric elements to the electronic scanner that converts the signals to an image, at least one uninsulated conductor in said second row together with said signal transmitting conductors, a second flexible conducting shield encircling the signal transmitting conductors and said at least one uninsulated conductor of the second row, the second flexible conducting shield defining an inner circumference within which the signal transmitting conductors and said at least one uninsulated conductor of the second row are free to move and to undergo flexure while the signal transmitting conductors of the second row engage both of the flexible conducting shields, the signal transmitting conductors of the second row tending to cross talk among themselves, both flexible conducting shields and the inner conductor being commoned together, circuitry between, first, the piezoelectric elements and, second, the signal transmitting conductors and said at least one uninsulated conductor of the second row, said at least one uninsulated conductor of the second row being connected to a ground bus on the circuitry to eliminate the need for connecting the shield to the ground bus, and the signal transmitting conductors of the second row each engaging both flexible conducting shields, and the signal transmitting conductors of the second row each further being purposely capacitance coupled with both flexible conducting shields to reduce cross talk among themselves.

5. A diagnostic probe assembly comprising:

multiple piezoelectric elements producing an array of scanned sound signals, at least one row of insulated, signal transmitting conductors for electrically connecting the piezoelectric elements to an electronic scanner that converts the sound signals to an image, at least one uninsulated conductor in said row together with said signal transmitting conductors, each of the signal transmitting conductors and at least one uninsulated conductor encircling a flexible inner conductor, a flexible conducting shield encircling the signal transmitting conductors and said at least one uninsulated conductor, the shield defining an inner circumference within which the signal transmitting conductors and said at least one uninsulated conductor are free to move and to undergo flexure while the signal transmitting conductors engage the shield and the inner conductor, the signal transmitting conductors tending to cross talk among themselves, the shield and the inner conductor being commoned together, circuitry between, first, the piezoelectric elements and, second, the signal transmitting conductors and said at least one uninsulated conductor, said at least one uninsulated conductor being connected to a ground bus on the circuitry to eliminate the need for connecting the shield to the ground bus, the signal transmitting conductors and said at least one uninsulated conductor each engaging both the inner conductor and the shield while being free to move in said inner circumference, and the signal transmitting conductors each further being purposely capacitance coupled with both the inner conductor and the shield to reduce cross talk among themselves.

6. A diagnostic probe assembly as recited in claim 5, wherein the signal transmitting conductors and said at least one uninsulated conductor extend helically over the flexible inner conductor.

7. A diagnostic probe assembly as recited in claim 5, wherein the signal transmitting conductors and said at least one uninsulated conductor helically extend over the flexible inner conductor, and the shield extends helically and encircles the signal transmitting conductors and said at least one uninsulated conductor.

8. A diagnostic probe assembly as recited in claim 5, and further comprising:

at least a second row of insulated, signal transmitting conductors electrically connecting respective piezoelectric elements to the electronic scanner that converts the signals to an image, at least one uninsulated conductor in said second row together with said signal transmitting conductors, a second flexible conducting shield encircling the signal transmitting conductors and said at least one uninsulated conductor of the second row, the second flexible conducting shield defining an inner circumference within which the signal transmitting conductors and said at least one uninsulated conductor of the second row are free to move and to undergo flexure while the signal transmitting conductors of the second row engage both of the flexible conducting shields, the signal transmitting conductors of the second row tending to cross talk among themselves, both flexible conducting shields and the inner conductor being commoned together, and connected to the ground or reference electrical potential, circuitry between, first, the piezoelectric elements and, second, the signal transmitting conductors and said at least one uninsulated conductor of the second row, said at least one uninsulated conductor of the second row being connected to a ground bus on the circuitry to eliminate the need for connecting the shield to the ground bus, and the signal transmitting conductors and said at least one uninsulated conductor of the second row each engaging both flexible conducting shields, and the signal transmitting conductors of the second row each further being purposely capacitance coupled with both flexible conducting shields to reduce cross talk among themselves.

* * * * *